United States Patent [19]
Cox

[11] Patent Number: 5,033,289
[45] Date of Patent: Jul. 23, 1991

[54] WATER CUT MONITORING MEANS AND METHOD

[75] Inventor: Percy T. Cox, Houston, Tex.

[73] Assignee: Texaco Inc., White Plains, N.Y.

[21] Appl. No.: 467,078

[22] Filed: Jan. 18, 1990

Related U.S. Application Data

[63] Continuation of Ser. No. 194,233, May 16, 1988, abandoned.

[51] Int. Cl.⁵ .......................................... G01R 27/26
[52] U.S. Cl. ................................. 73/61/1 R; 324/689
[58] Field of Search .................... 73/61.1 R, 61 R, 53; 324/664, 665, 689

[56] References Cited

U.S. PATENT DOCUMENTS

| | | | |
|---|---|---|---|
| 3,515,988 | 6/1970 | Shawhan | 73/61.1 R X |
| 3,816,811 | 6/1974 | Cmelik | 324/689 X |
| 4,240,028 | 12/1980 | Davis, Jr. | 324/665 |
| 4,266,188 | 5/1981 | Thompson | 73/61.1 R X |
| 4,340,938 | 7/1982 | Rosso | 73/61.1 R X |
| 4,751,842 | 6/1988 | Ekrann et al. | 73/61.1 R |
| 4,774,680 | 9/1988 | Agar | 73/61.1 R X |

*Primary Examiner*—Hezron E. Williams
*Assistant Examiner*—Joseph W. Roskos
*Attorney, Agent, or Firm*—Robert A. Kulason; James J. O'Loughlin; Ronald G. Gillespie

[57] ABSTRACT

Apparatus monitors the water cut of a petroleum stream flowing in a pipeline by comparing a probe signal to a reference signal. A probe is located in the pipeline and is connected to the reference signal through a series resistance. The probe signal changes as a function of the impedance of the petroleum stream. A circuit measures the changes in the probe signal, compares the changes to the reference signal and derives a water cut value for the petroleum stream based on these measurements.

14 Claims, 4 Drawing Sheets

WATER CUT MONITORING MEANS AND METHOD

This is a continuation of application Ser. No. 07/194,233, filed May 16, 1988, now abandoned.

BACKGROUND OF THE INVENTION

FIELD OF THE INVENTION

The present invention relates to monitoring means and method in general and, more particularly, to water cut monitoring means and methods.

SUMMARY OF THE INVENTION

Apparatus monitors the water cut of a petroleum stream flowing in a pipeline by comparing a probe signal to a reference signal. A probe is located in the pipeline and is connected to the reference signal through a series resistance. The probe signal changes as a function of the impedance of the petroleum stream. A circuit measures the changes in the probe signal, compares the changes to the reference signal and derives a water cut value for the petroleum stream based on these measurements.

The objects and advantages of the invention will appear more fully hereinafter from a consideration of the detailed description which follows, taken together with the accompanying drawings where in one embodiment the invention is illustrated by way of example. It is to be expressly understood, however, that the drawings are for illustration purposes only and are not to be construed as defining the limits of the invention.

DESCRIPTION OF THE INVENTION

The measurement of water cut, or percent water, is essential in the determination of the quantities of oil and water produced by a well. By combining water cut and flow rate data, production can be described in terms of barrels of oil per day and barrels of water per day. Flowmeters are commercially available which makes an adequate measurement of flow rate provided most of the gas present in the produced fluid is removed.

A number of commercial water-cut meters are also available. The majority of these meters are designed for use only when the oil/water mixture is oil continuous, i.e. when any water present is suspended within the oil. These meters function purely as a capacitance measurement and operate properly only when a relatively high impedance exists across the measurement electrodes. When the fluid phase is water continuous, i.e. when the oil is suspended within the water, a conducting path exists across the electrodes which effectively "shorts out" the capacitance measurement. This shorting effect is highly sensitive to salinity and temperature and this renders capacitance probes useless when only a few parts per million of salt are present.

The present invention is proposed for use in oil fields where produced fluids are diverted into a test tank for gauging. In most cases, the initial fluid pumped from the tank is essentially 100% water. A measurement of probe phase angle is made during the time the fluid is 100% water and this value is stored and used as a reference during the entire pumpout of the tank. This value represents a measurement of the water resistivity ($R_w$) of the fluid since no oil is present.

As the oil/water emulsion flows through the probe, the phase angle or voltage across the probe is measured and compared with the previously measured value obtained during 100% water flow. By cross-plotting these two values, an accurate measurement of water-cut is obtained.

The present invention is a water cut monitor which accurately measures percent water during both fluid phases and reduces the need for adding heat and chemicals to the produced fluid in order to obtain separation of the water and oil. In addition, the necessity for the fluid to settle for several hours is eliminated.

Figure 1A:
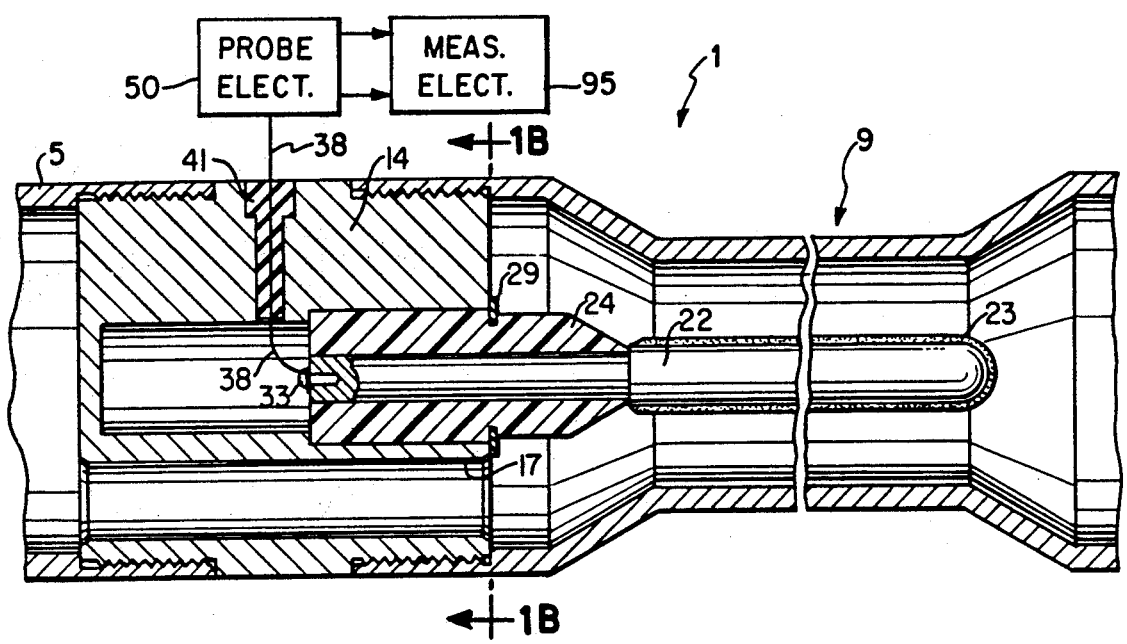
FIG. 1A is a representation drawing of a water cut monitoring system constructed in accordance with the present invention.
Figure 1B:
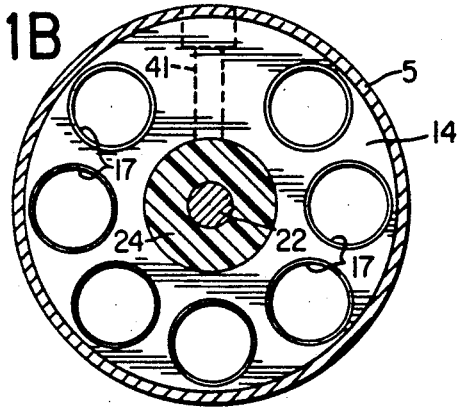
FIG. 1B is a cross-sectional view taken along the line A—A in FIG. 1A.

Referring now to FIGS. 1A and 1B, there is shown a sensing unit 1 mounted in the pipeline 5 having a constriction section 9. Sensing unit 1 has a support body 14 having a plurality of channels 17 passing through it to permit flow of the petroleum stream through support body 14. Support body 14 provides for rigid mounting of a probe 22 which is mounted within a probe housing 24 made of non-conductive material. Probe 22 has two diameters. That portion of probe 22 extending outside of probe housing 24 has a larger diameter, while that portion of probe 22 located within housing 24 has a small diameter. Probe housing 24 is held in support body 14 by a brass fitting 29. A terminal 33 is affixed to probe 22 and has an electrical wire 38 connected thereto so that there is an electrical connection between probe 22 and probe electronics 50 as hereinafter described. Wire 38 passes through an insulator 41 located in support body 14 permitting wire 38 to pass from probe 22 to side of the sensing unit 1. Probe 22 is made of aluminum and is coated on its entire surface with a 0.010 inch thickness coating 23 of Halar, Teflon or ceramic insulation.

Figure 2:
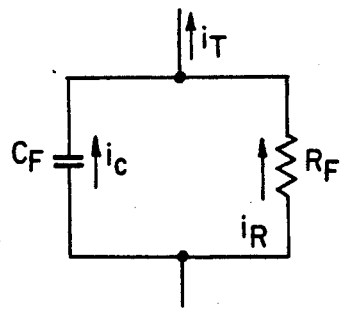
FIG. 2 is a simplified schematic of an equivalent circuit representing the resistance and capacitance of a petroleum stream.

At this time it is probably better to discuss the electrical effects of the petroleum stream on probe 22. With reference to FIG. 2, there is shown an equivalent circuit of a water-continuous petroleum stream. As can be seen, the petroleum stream has a capacitance of $C_F$ and resistance $R_F$ connected in parallel and which an electric current $i_c$ flows through capacitor $C_F$ and electric current $i_R$ flows through resistor $R_F$ their vector sum being $i_T$, the total electrical current through the fluid. It can be appreciated in regards to FIG. 2 that standard commercial capacitance-type water cut meters operate at a fairly low frequency, usually in the 100 KHz to 1000 KHz range. At these low frequencies, the capacitive reactance of the fluid is quite high and because the fluid is water continuous, a conductive path exists across the capacitance electrodes. However, only a relatively small number of conductive ions in the water will effectively short out the capacitive measurement. This explains why commercial meters do not function in water-continuous petroleum streams.

In the present invention, by using a high operating frequency in the range of 10 MHz up to 200 MHz and particularly at a preferred frequency of 20 MHz, the capacitive reactance decreases. Operation at the higher frequencies causes the capacitive reactance to be the same order of magnitude as the fluid resistance, $R_F$.

Figure 3A:
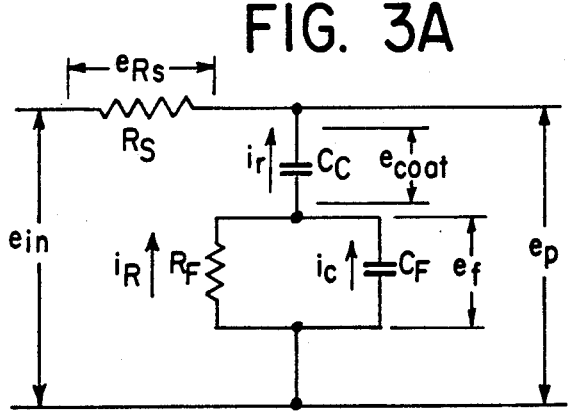
FIG. 3A is a schematic diagram of an equivalent circuit representing the measurement of a water-continuous phase petroleum stream.
Figure 3B:
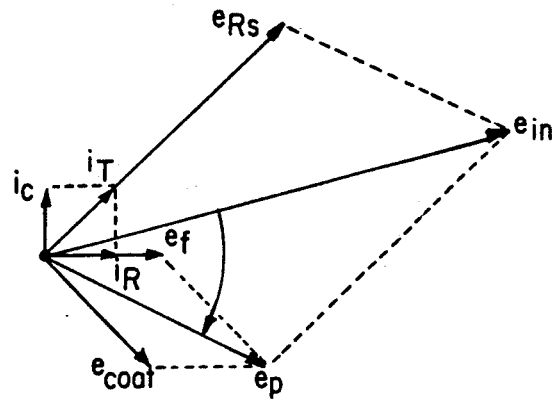
FIG. 3B is a vector diagram of voltages and currents occurring in the equivalent circuit of FIG. 3A.

With reference now to FIGS. 3A and 3B, FIG. 3A shows the equivalent circuit of probe 22 for a water continuous petroleum stream, while FIG. 3B shows a vector diagram of the voltages and currents occurring in the equivalent circuit for this condition. Again, $R_F$ and $C_F$ represent the fluid resistivity and capacitance, respectively, as before. Capacitance $C_C$ represents the capacitance of coating 23 on probe 22. By making coating 23 as thin as is practical, capacitance $C_C$ can be made large, and thus the reactance $X_C$ is quite small. It was found that 0.010 inch coating of Halar worked well in this application. The resistance $R_S$ provides isolation of the probe from the signal source providing the voltage $e_{in}$. The preferred measurement is the phase angle between voltage $e_{in}$ and the probe voltage $e_p$.

When a voltage across the fluid ($e_f$) is assumed as a reference, the conductive current ($i_R$) would be in phase with $e_f$ and the capacitive current ($i_c$) would be 90 degrees ahead of $e_f$ as shown. The sum of these two currents result in the total current $i_T$ which passes through capacitance $C_C$ and generates the voltage $e_{coat}$ which falls 90 degrees behind it. The vector sum of $e_{coat}$ and $e_f$ yields $e_p$, the voltage across the probe. The current $i_T$ also generates a voltage across the series resistance $R_F$ which is $e_{Rs}$. Finally, the vector sum of $e_{Rs}$ and $e_p$ results in the generation of the input voltage, $e_{in}$. The phase angle between $e_{in}$ and $e_p$, shown in the vector diagram of FIG. 3B is the preferred measurement used to obtain water cut by this method.

Figure 4A:
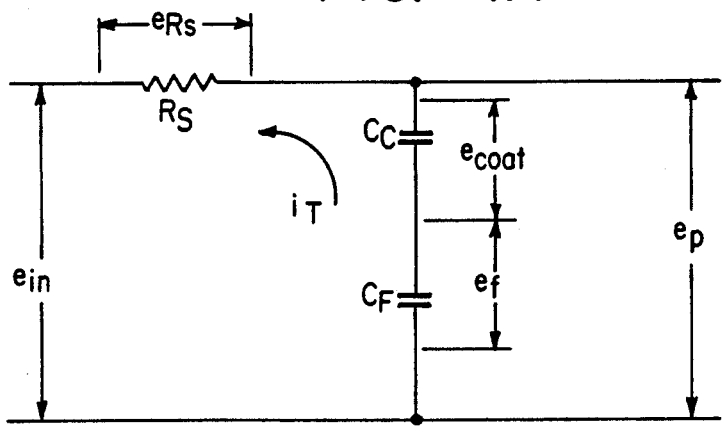
FIG. 4A is a schematic diagram of an equivalent circuit for the measuring of an oil-continuous phase petroleum stream.
Figure 4B:
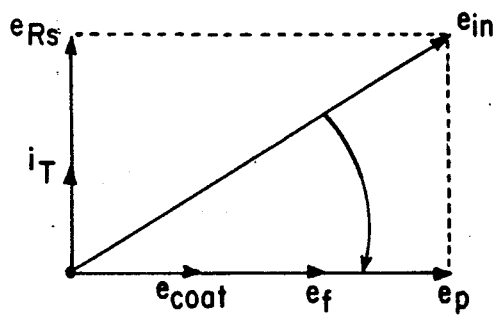
FIG. 4B is a vector diagram of the currents and voltages occurring in FIG. 4A.

With regard to the oil-continuous phase measurement, FIG. 4A shows the equivalent circuit for probe 22 while an associated vector diagram is depicted in FIG. 4B. The oil-continuous measurement of water cut is much easier to achieve because no continuous conductive path exists within the emulsion and therefore salinity change does not have a significant effect on the measurement. The probe is represented by a fluid capacitance, $C_F$ in series with coating 23 capacitance $C_C$. As before, the resistance $R_S$ provides isolation of the signal source and probe 22. An increase in water cut causes capacitance $C_F$ to increase and the reactants of capacitance $C_F$ to decrease. This increases the current, $i_T$ and thus increases $e_{Rs}$. Because $e_{in}$ is the vector sum of $e_{Rs}$ and $e_p$, this causes an increase in the phase angle between $e_{in}$ and $e_p$.

Figure 5:
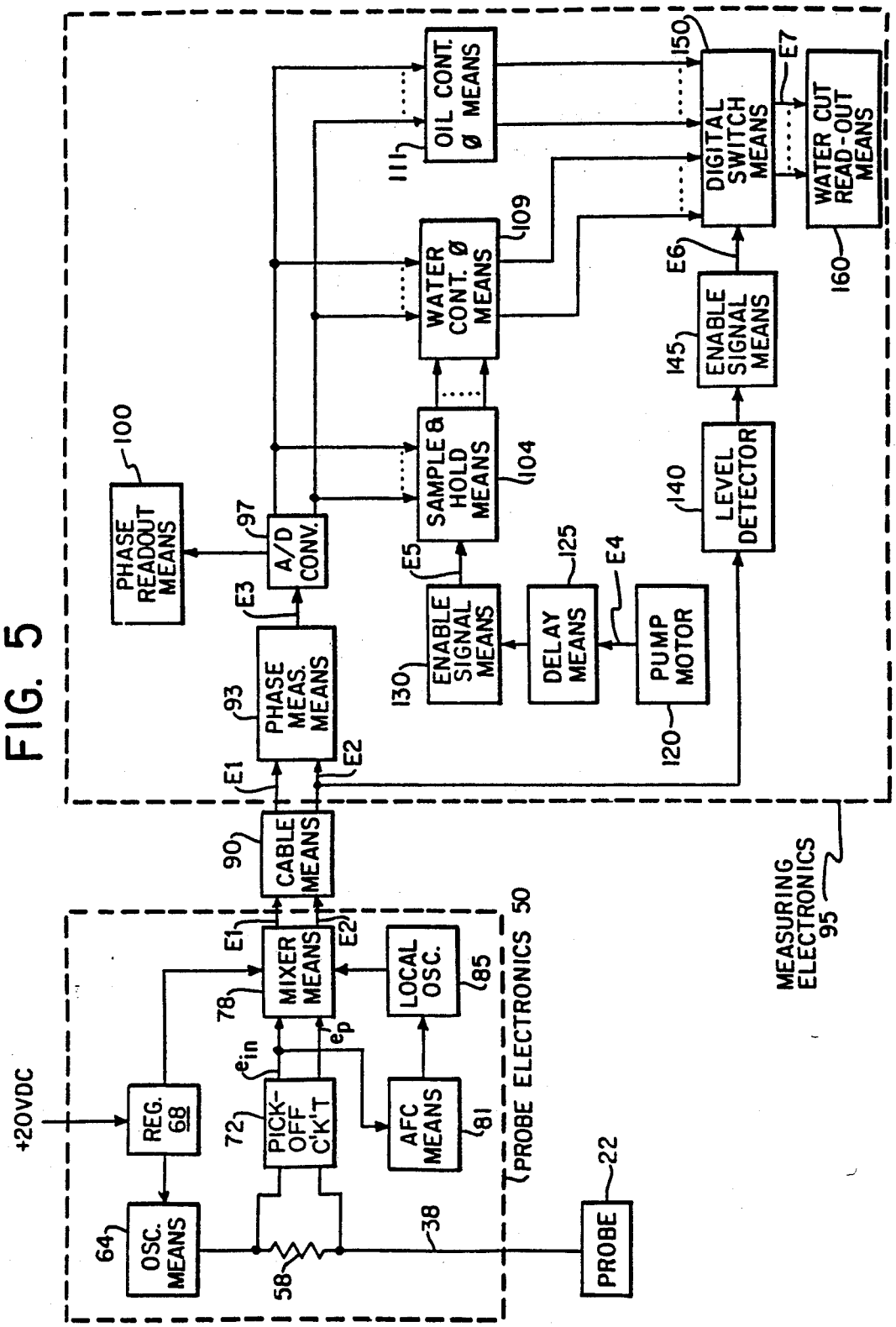
FIG. 5 is a simplified block diagram of a water cut monitor constructed in accordance with the present invention.

With reference to FIGS. 1 and 5, there is shown probe electronics 50 as including electrical wire 38 connecting probe 22 to a resistor 58 which is the $R_S$ of the equivalent circuit shown in FIGS. 3A and 4A. Resistor 58 is connected to oscillator means 64 providing the 20 MHz operating signal to probe 22.

A regulator 68 receives a plus 20 volt DC and provides a regulated voltage to oscillator means 64.

A pick-off circuit 72 connected across resistor 58 provides a reference signal $e_{in}$ and a probe signal $e_p$ to mixer means 78. Mixer means 78 also receives a regulated power voltage from regulator 68. Signal $e_{in}$ from probe circuit 72 is provided to automatic frequency control means 81 which in turn provides a frequency control signal to a local oscillator 85. Local oscillator 85 provides a 19.998 MHz signal to mixer means so that mixer means 78 provides two signals E1 and E2 corresponding to signals $e_{in}$ and $e_p$, respectively at 2 KHz.

Signals E1 and E2 are provided to coaxial cable means 90. Cable means 90 provides signals E1, E2 to phase measurement means 93 in measuring electronics 95, which determines the phase difference between signals E1, E2 and provides a phase signal E3 to an analog-to-digital converter 97. Analog-to-digital converter 97 provides a digital signal to phase readout means 100, and digital signals to sample and hold means 104, water continuous phase means 109 and oil continuous phase means 111. The digital signal provided to phase readout means 100 is used for calibration purposes.

Figure 6:
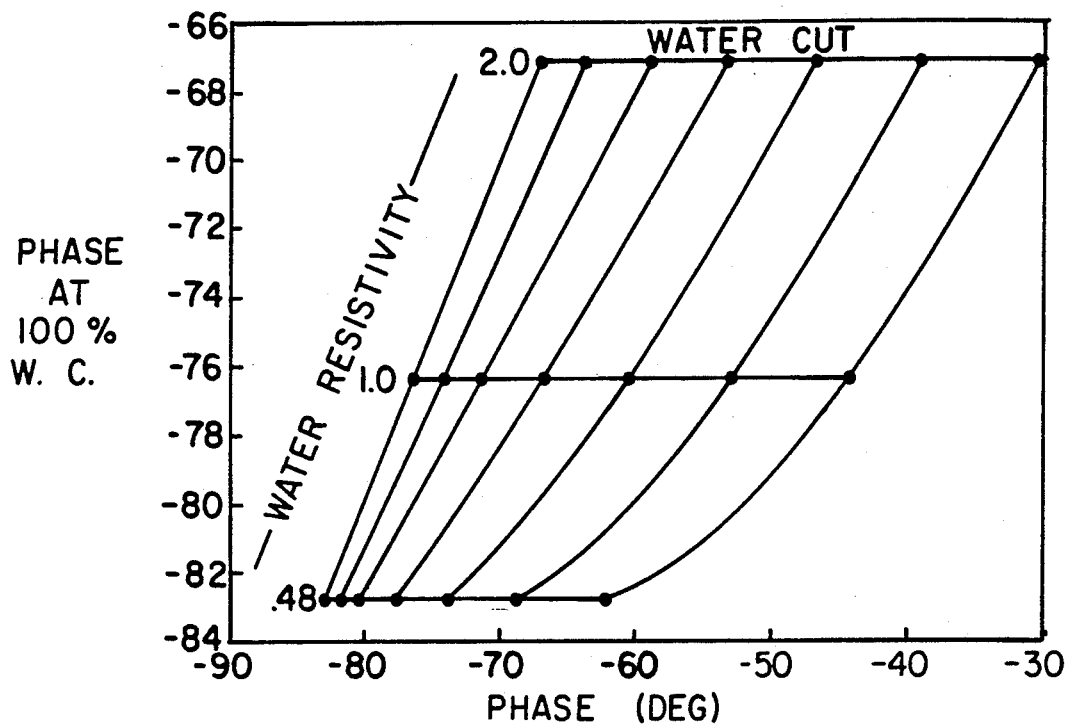
FIG. 6 is a plot of water cut curves for a water continuous phase petroleum stream for a particular temperature.
Figure 7:
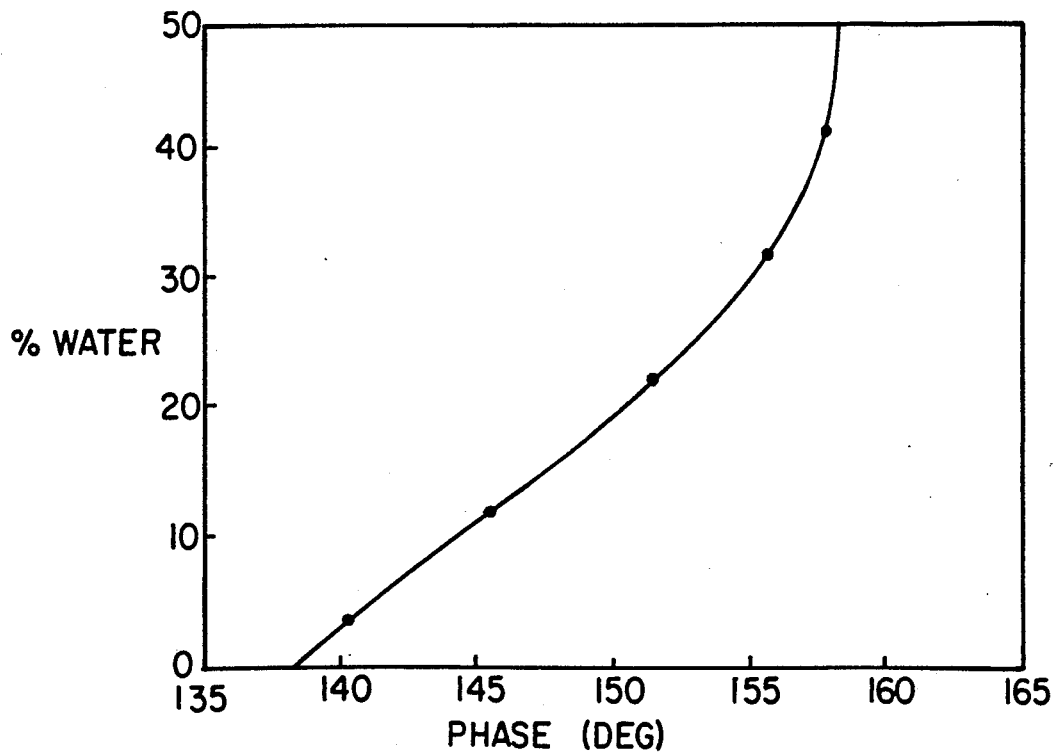
FIG. 7 is a plot of water cut curves for an oil continuous phase petroleum stream.

Water continuous phase means 109 is an EPROM memory having data stored within related to the curves shown in FIG. 6. Oil continuous phase means 111 is also an EPROM memory having data stored within related to the curve shown in FIG. 7. Water continuous phase means 109 is controlled by the digital phase signals from analog-to-digital converter 97 to provide a water continuous output signal corresponding to the water cut of the petroleum stream. Oil continuous phase means 111 is controlled by the digital phase signal to provide an oil continuous output signal corresponding to the water cut of the petroleum stream. Obviously, since the petroleum stream sensed by probe 22 can only be in one phase, one of the water cut signals is erroneous. The selection of the correct water cut signal will be discussed hereinafter.

Water continuous measurement is accomplished by action of the EPROM within water-continuous phase means 109. When the test cycle begins, the pump motor 120 provides a signal E4 to delay means 125 which provides a few seconds delay for any oil left in the probe from the previous measurement to be flushed out by water pumped at the start of the current measurement. After this delay, an enable gate is generated by enable signal means 130. The resulting enable signal E5 is applied to sample and hold means 104 which then samples and holds the digital phase value being provided by analog-to-digital converter 97. Since the fluid being pumped from the tank is all water at the beginning of the test, the signal E5 represents a 100% water cut value and corresponds to an entry on the vertical axis of the plot in FIG. 6. Since this 100% water cut value is determined "at temperature", the need for temperature compensation or correction is eliminated.

Signal E2, which corresponds to the signal from probe 22, is provided to a level detector 140 which in turn provides a signal to enable signal means 145. Signal E2 is at a high level when the petroleum has an oil continuous phase. The high level of signal E2 causes level detector 140 to control enabling means 145 to provide a control signal E6 to digital switch means 150. Digital switch means, receiving the digital signals from water continuous phase means 109 and oil continuous phase means 111, is affected by control signal E6 to select one set of received digital signals to be provided as water cut signal E7 which is provided to water cut readout means 160.

Since the condition just specified was that signal E2 is at a high level due to the petroleum stream being in the oil-continuous phase, digital switch 150 selects the digital signals from oil-continuous phase means 111 to be provided as digital signals E7. When signal E2 drops below a predetermined value, level detector 140 no longer provides a high level signal to enable signal means 145, so that signal E6 is now at a low logic level causing digital switch means 150 to pass the digital signals from water continuous phase means 109 as water cut digital signals E7.

What is claimed is:

1. A monitor which monitors the water cut of a petroleum stream flowing in a pipeline comprising:
    source means for providing a reference signal,
    probe means located in the pipeline and receiving the reference signal for affecting the reference signal as a function of the impedance of the petroleum stream,
    signal means cooperating with the source means and the probe means for providing signals E1 and E2 representative of the affecting of the reference signal by the probe means, and
    deriving means connected to the signal means for deriving the water cut of the petroleum stream in accordance with the signals E1 and E2; and
    in which the probe means includes:
    a capacitive probe,
    a resistor connecting the source means to the capacitive probe, and
    a housing for maintaining the probe in the pipeline; and
    the signal means includes:
    pick-off circuit means connected across the resistor of the probe means and providing two signals $e_{in}$ and $e_p$, which correspond to the unaffected reference signal and to the affected reference signal, respectively,
    mixer means connected to the pick-off means for providing signals E1 and E2 in accordance with signals $e_{in}$ and $e_p$,
    automatic frequency control means connected to the probe means and receiving signal $e_{in}$ for improving a frequency control signal, and
    local oscillator means connected to the automatic frequency control means and to the mixer means providing a signal at a predetermined frequency to the mixing means in accordance with the frequency control signal from the automatic frequency control means.

2. A monitor as described in claim 1 in which the probe includes:
    a body of conductive material a first portion of which is located in the housing and a second portion of which is located in the flowing petroleum stream, and
    a coating of non-conductive material covering at least the portion of the body of conductive material located in the petroleum stream.

3. A monitor as described in claim 2 in which the deriving means includes:
    phase means connected to the mixer means for providing a phase signal in accordance with a phase difference between signals E1 and E2,
    means for providing a water signal corresponding to an average 100 percent water content,
    water cut means connected to the phase difference means for providing two signals in accordance with the phase signal and the average 100 percent water signal, one signal being a water continuous water cut signal representing the water cut for the petroleum stream being in a water continuous phase, the other signal being an oil continuous water cut signal corresponding to the water cut for the petroleum stream in an oil continuous phase, and
    output means connected to the mixer means and to the water cut means for selecting one of the water cut signals to be provided as an output signal corresponding to the water cut of the petroleum stream in accordance with signal E2 from the mixer means.

4. A monitor as described in claim 3 in which the water cut means includes:
    first memory means having predetermined data stored therein relating the phase signal and the average 100 percent water content signal to the water cut of the petroleum stream for providing the water continuous water cut signal, and
    second memory means connected to the phase difference means and having data stored therein relating phase differences to water cut for providing the oil-continuous water cut signal.

5. A monitor as described in claim 4 in which the output means includes:
    a level detector receiving signal E2 from the mixer means for providing a signal when signal E2 exceeds a predetermined level,
    enabling means connected to the level detector for providing an enabling pulse in accordance with the signal from the level detector, and
    switching means connected to the enabling means for selecting either the water continuous phase water cut signal or the oil continuous phase water cut signal in accordance with the enabling signal to be provided as the output signal.

6. A monitor as described in claim 5 in which the 100 percent water-continuous average signal means includes:
    delay means receiving a signal indicative that a pump motor has started pumping the petroleum stream through the pipeline for delaying that signal a predetermined time interval,
    second enabling signal means connected to the delay means for providing an enabling pulse,
    sample and hold means connected to the phase means and to the water continuous phase memory means for sampling, holding and averaging the phase difference signal for the time that the fluid in the pipeline is 100 percent water and for providing the water signal to water continuous phase memory means.

7. A monitor as described in claim 5 further including:
    readout means connected to the switching means for providing a readout of the output signal received from the switch means.

8. A monitoring method which monitors the water cut of a petroleum stream flowing in a pipeline comprising the steps of:
   providing a reference signal,
   affecting the reference signal as a function of the impedance of the petroleum stream,
   providing signals E1 and E2 representative of the affecting of the reference signal by probe means, and
   deriving the water cut of the petroleum stream in accordance with the measurement of signals E1 and E2; and
   in which the affecting step includes:
   placing a capacitive probe in the petroleum stream,
   providing the reference signal to the capacitive probe through a resistor, and
   supporting the probe in the pipeline with a housing; and
   the E1, E2 signal step includes:
   picking off a voltage and current across the resistor of the probe means,
   providing two signals $e_{in}$ and $e_p$, which correspond to the unaffected reference signal and to the affected probe signal, respectively, in accordance with the picked off voltage and current,
   providing signals E1 and E2 with mixer means in accordance with signals $e_{in}$, and $e_p$, and
   providing a signal at a predetermined frequency to the mixing means in accordance with the frequency control signal.

9. A method as described in claim 8 in which the capacitive probe step includes:
   using a body of conductive material, a first portion of which is located in the housing and a second portion of which is located in the flowing petroleum stream, and
   coating covering the second portion of the body of conductive material with non-conductive material.

10. A method as described in claim 9 in which the deriving step includes:
    providing a phase signal in accordance with a phase difference between signals E1 and E2,
    providing a water signal corresponding to an average 100 percent water content of the petroleum stream,
    providing two water cut signals in accordance with the phase signal and the average 100 percent water signal, one signal being a water continuous phase water cut signal representing the water cut for the petroleum stream being in a water continuous phase, the other signal being an oil continuous water cut signal corresponding to the water cut for the petroleum stream in an oil continuous phase and
    selecting one of the water cut signals to be provided as an output signal corresponding to the water cut of the petroleum stream in accordance with signal E2 from the mixer means.

11. A monitor as described in claim 10 in which the water cut signal step includes:
    first memory means storing first predetermined data relating to the phase signal and the average 100 percent water content signal to the water cut for the water continuous phase of the petroleum stream,
    providing the water continuous water cut signal in accordance with the stored first predetermined data and the phase signal,
    storing second predetermined data relating to the phase signal to water cut for the oil continuous phase, and
    providing the phase continuous water cut signal in accordance with the stored second predetermined data and the phase signal.

12. A method as described in claim 11 in which the selecting step includes:
    detecting the level of signal E2 from the mixer means,
    providing a signal when signal E2 exceeds a predetermined level,
    providing an enabling pulse in accordance with the signal from the level detecting step, and
    selecting either the water continuous phase water cut signal or the oil continuous phase water cut signal in accordance with the enabling signal to be provided as the output signal.

13. A method as described in claim 12 in which the 100 percent water content average signal step includes:
    receiving a signal indicative that a pump motor has started pumping the petroleum stream through the pipeline,
    delaying the received signal a predetermined time interval,
    second enabling signal means connected to the delay means for providing an enabling pulse in accordance with the delayed received signal,
    sampling, holding and averaging the phase signal in accordance with the enabling pulse, and
    providing the water signal.

14. A method as described in claim 12 further in providing a readout of the output signal.

* * * * *